United States Patent
Bálint et al.

(10) Patent No.: US 7,381,835 B2
(45) Date of Patent: Jun. 3, 2008

(54) RESOLUTION PROCESS FOR (R)-(-)-2-HYDROXY-2-(2-CHLOROPHENYL) ACETIC ACID

(75) Inventors: József Bálint, Budapest (HU); Marianna Csatáriné Nagy, Budapest (HU); Zsolt Dombrády, Budapest (HU); Elemér Fogassy, Budapest (HU); Antal Gajáry, Budapest (HU); Charles Suba, Sisteron (FR)

(73) Assignee: Sanofi-Aventis, Paris (FR)

( * ) Notice: Subject to any disclaimer, the term of this patent is extended or adjusted under 35 U.S.C. 154(b) by 360 days.

(21) Appl. No.: 10/480,562

(22) PCT Filed: Jun. 14, 2002

(86) PCT No.: PCT/HU02/00054

§ 371 (c)(1),
(2), (4) Date: Jun. 25, 2004

(87) PCT Pub. No.: WO03/000636

PCT Pub. Date: Jan. 3, 2003

(65) Prior Publication Data

US 2004/0242921 A1    Dec. 2, 2004

(30) Foreign Application Priority Data

Jun. 21, 2001    (HU)    .................................... 0102567

(51) Int. Cl.
*C07B 57/00*    (2006.01)

(52) U.S. Cl. .................................... 562/401

(58) Field of Classification Search ................. 562/401
See application file for complete search history.

(56) References Cited

FOREIGN PATENT DOCUMENTS

| EP | 0 340 663 | 11/1989 |
|---|---|---|
| JP | 61-115052 | 6/1986 |
| JP | 2-138237 | 5/1990 |
| JP | 85-03949 T | 4/1996 |
| JP | 10-237013 | 9/1998 |
| JP | 01-072644 | 3/2001 |
| JP | 2002114737 | 4/2002 |
| WO | WO 94/12451 | 6/1994 |

OTHER PUBLICATIONS

Riebsomer et al , J. of American Chemical Society, 1938, vol. 60. p. 1015-1016.*
Berge et al, J. of Pharamceutical Sciences, Jan. 1977, vol. 66, No. 1. p. 1-18.*
Derwent Abstract No. 475211 (2002).
Blaschke et al, English language abstract of corresponding EP 0 340 663.
Hasegawa et al, English language abstract of corresponding JP 51-115052.
Nakamoto et al, English language abstract of corresponding JP 10-237013.
Noda et al, English language abstract of corresponding JP 01-072644.

* cited by examiner

*Primary Examiner*—Taylor Victor Oh
(74) *Attorney, Agent, or Firm*—Paul R. Darkes

(57) ABSTRACT

The subject of the present invention is the preparation of the (R)-(-)-2-hydroxy-2-(2-chlorophenyl)acetic acid of the formula (I) by the resolution of the corresponding racemic compound by using the compounds of the general formula (II).

15 Claims, 1 Drawing Sheet (I)

(I)

(II)

RESOLUTION PROCESS FOR (R)-(−)-2-HYDROXY-2-(2-CHLOROPHENYL) ACETIC ACID

Figure 1:
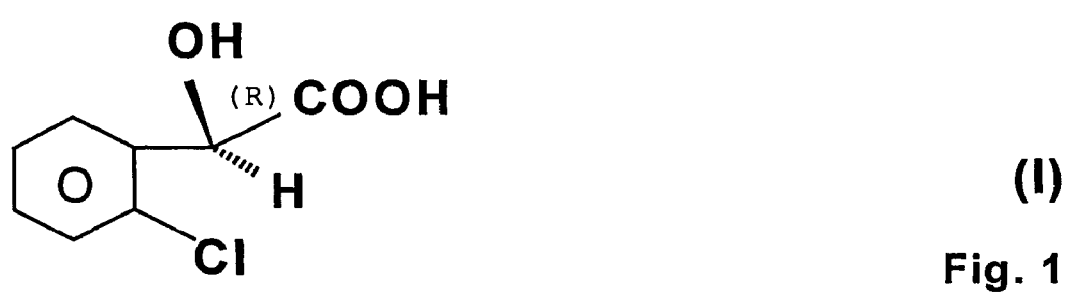

The object of the present invention is a new resolution process of the racemic 2-hydroxy-2-(2-chlorophenyl)-acetic acid which makes possible the preparation of (R)-(−)-2-hydroxy-2-(2-chlorophenyl)acetic acid of the formula (I).

The optically active compound of the formula (I) is one of the starting materials of the known optically active trombocyta antiaggregant compound clopidogrel (Plavix®) (WO-99/18110).

The racemic 2-hydroxy-2-(2-chlorophenyl)acetic acid may be obtained by different processes/Chem. Ber. 37 S. 3173 (1904), J. Am. Chem. Soc. 55 p 2593 (1933), Chem. Ber. 92 S 1739 (1959)/. Several processes are known for the preparation of the optically active compound of the formula (I) from the literature (Chirality 7 (8) p 652-76 (1995), Bull. Soc. Chim. Fr. (1973) 12, Pt 2, 3330) but they have drawbacks from the industrial point of view because they either use expensive resolution agents (alkaloids) or they applied microbiological processes requiring large volumes and their productivity is low. (EP-A-610048, EP-A-449648, EP-A-527553). It was aimed to find a more advantageous chemical process than the known ones which give a technically simpler and cheaper process for the preparation of the compound of the formula (I).

Unexpectedly we found that the compounds of the general formula (II) form a poorly soluble salt with only one enantiomer or racemic 2-hydroxy-2-(2-chlorophenyl)acetic acid and thus one of the enantiomers may be selectively removed from the reaction mixture of the resolution process.

According to the invention the compound of the formula (I) is yielded from its solid diastereomeric salt formed with a compound of the general formula (II) or it is yielded from the mother liquor of the resolution process and optionally its optical purity is increased by selective recrystallization.

The process according to the invention may be carried out preferably in an organic solvent for example in methanol or a mixture of water and an organic solvent for example in a water—ethylacetate or a water—methanol or an isopropyl acetate—methanol—water mixture.

As a compound of the general formula (II) the (1S, 2S)-(+)-1-phenyl-2-amino-1,3-propane-diol, (1R, 2R)-threo-(−)-1-(4-nitrophenyl)-2-amino-1,3-propane-diol or the L-(+)-lysine are applicable the most preferably. (Aldrich Cat. No. L-(+)-lysine: 16971-4 (2000-1); (1S, 2S)-(+)-1-phenyl-2-amino-1,3-propane-diol: 18564-6(2000-1); (1R, 2R)-threo-(−)-1-(4-nitrophenyl)-2-amino-1,3-propane-diol: A 7070-4 (2000-1)).

The compounds of the general formula (II) are generally used in an equimolar ratio counted to the racemic acid.

The resolution process is carried out preferably between 10° C. and 30° C. The optical purity of the crude compound of the formula (I) thus obtained is 84-98%. The compound of the formula (I) in almost 100% optical purity may be received by a recrystallization of the crude compound of the formula (I) at 40-100° C. using toluene or isopropyl-acetate as solvent. The solvent is used between 1.5-10 volumetric units preferably 6-8 volumetric units counted on a mass unit of the compound to be recrystallized.

Another object of the present invention are salts of the compound of the formula (I) formed with compounds of the general formula (II).

Efficiency of this invented process is increased by the decomposition of the diastereometric salt formed from (S)-(+)-2-hydroxy-2-(2-chlorophenyl)acetic acid and from a compound of the general formula (II), the (S)-(+)-isomer is racemized and it is resolved again according to the present invention.

The racemisation process is a further object of the present invention.

Thus the starting racemic compound can be transformed into the desired enantiomer almost in full extent.

The racemisation can be carried out in the presence of a base, preferably aqueous sodium-hydroxyde or potassium-hydroxyde may be used. The use of a small amount of aprotic solvent in the aqueous medium accelarate the racemisation process. Preferred aprotic solvents are dimethysulfoxide, sulfolane, dimethylformamide, hexamethylphosphotriamide or the N-methyl-pyrrolidone. The racemisation is made preferably at the boiling point of the reaction mixture in the presence of 0.1-0.5 volumetric units of aprotic solvent. Further details of the present invention are shown in the following examples without limiting our claims to their content.

EXAMPLE 1

Resolution of racemic 2-hydroxy-2-(2-chlorophenyl)-acetic acid by (1S, 2S)-(+)-1-phenyl-2-amino-1,3-propane diol (The compound of the general formula (II)—wherein $R^1$ is a hydroxy-methyl group, $R^2$ is a phenyl group, $R^3$ is a hydroxy group) Racemic 2-hydroxy-2-(2-chlorophenyl)acetic acid (20.0 g 107 mmol) was dissolved in 60 cm³ of ethylacetate saturated with water and (1S, 2S)-(+)-1-phenyl-2-amino-1,3-propane-diol (18.0 g 107.5 mmol) was added thereto and then the mixture was seed by a salt formed from (S)-(+)-2-hydroxy-2-(2-chlorophenyl)acetate and (1S, 2S)-(+)-1-phenyl 2-amino-1,3-propane-diol at room temperature.

The mixture was stirred for 3 hours at room temperature, the precipitated substance was filtered off and it was washed with ethyl-acetate and it was dried: 30.7 g of white crystalline substance were received. This substance was dissolved in a mixture of 50 cm³ of water and 15 cm³ of 37% hydrochloric acid and it was extracted with methyl-tert.butyl-ether. The extract was dried on sodium-sulfate and the solvent was evaporated: 15.3 g of enantiomeric mixture rich in (S)-(+)-2-hydroxy-2-(2-chlorophenyl)acetic acid were obtained ($[\alpha]_D^{20}=+38°$ (c=4, methyl alcohol/, optical purity is 24%) which can be racemized according to Example 4 and recycled into the process.

The mother liquor obtained from the resolution was concentrated, dissolved in the mixture of 15 cm³ of water and 4.0 cm³ of 37% hydrochloric acid and it was extracted with methyl-tert.-butyl-ether. The combined extracts were dried on sodium sulfate and concentrated: 4.3 g of (R)-(−)-2-hydroxy-2-(2-chlorophenyl)acetic acid were obtained ($[\alpha]_D^{20}=-132.2°$ (c=4, methyl-alcohol) with optical purity of 84.2%. This product was recrystallized from toluene, it was filtered at 60° C., washed with toluene. After drying 3.62 g (19.4 mmol 18.1%) of R-(−)-2-hydroxy-2-(2-chlorophenyl)acetic acid were obtained ($[\alpha]_D^{20}=-157°$ (c=4, methyl-alcohol).

EXAMPLE 2

Resolution of racemic 2-hydroxy-2-(2-chlorophenyl)acetic acid by (1R, 2R)-(−)-threo-1-(4-nitrophenyl)-2-amino-1,3-propane-diol) (compound of the general formula (II)

wherein $R^1$ is a hydroxymethyl group, $R^2$ is a p-nitrophenyl group, $R^3$ is a hydroxy group)

Racemic 2-hydroxy-2-(2-chlorophenyl)acetic acid (20.0 g 107 mmol) was dissolved in a mixture of 120 g of isopropyl acetate, 16 cm$^3$ of methanol and 2 cm$^3$ of water.

22.8 g (107 mmol) of (1R, 2R)-(−)-threo-1-(4-nitrophenyl)-2-amino-1,3-propane-diol were added thereto during mild heating to help the dissolution. At room temperature the mixture was seeded with salt of (1R, 2R)-(−)-threo-1-(4-nitrophenyl)-2-amino-1,3-propane-diol formed with R-(−)-2-hydroxy-2-(2-chlorophenyl)acetic acid. The reaction mixture was stirred for 3 hours at room temperature and the precipitated substance was filtered off, washed and dried, 13.6 g of crystalline substance were obtained, which is the salt of the above diol and the (R)-(−)-2-hydroxy-2-(2-chlorophenyl)acetic acid.

This salt was dissolved in 20 cm$^3$ of water and the solution was acidified by 5.7 cm$^3$ of concentrated hydrochloric acid and it was extracted with methyl-tert.-butylether, the extracts were combined, dried, concentrated and 5.84 g (31.3 mmol) of crude (R)-(−)-2-hydroxy-(2-chlorophenyl)acetic acid were obtained ($[\alpha]_D^{20}=-151°$ (c=4, methyl alcohol), its optical purity is 96%.

This crude acid was recrystallized from 41 cm$^3$ of toluene at 60° C. and the product was dried. The weight of (R)-(−)-2-hydroxy-2-(2-chlorophenyl)acetic acid is 5.6 g (30.0 mmol). Yield is 28%. ($[\alpha]_D^{20}=-157°$ (c=4, methyl alcohol).

The mother liquor of the resolution was concentrated, dissolved in 40 cm$^3$ of water, acidified with 12.3 cm$^3$ of 37% hydrochloric acid and it was extracted with methyl-tert.-butylether and the obtained substance rich in (S)-(+)-2-hydroxy-2-(2-chlorophenyl)acetic acid which is an enantiomeric mixture is 13.8 g (73.95 mmol) ($[\alpha]_D^{20}=+61°$ (c=4, methyl alcohol), optical purity is 39%. This substance is racemisable and its recyclation into the process is possible.

EXAMPLE 3

Resolution of racemic 2-hydroxy-2-(2-chlorophenyl)acetic acid with L-(+)-lysine (compound of the general formula (II)—wherein $R^1$ is a carboxyl group, $R^2$ is a 3-amino-propyl group and $R^3$ is a hydrogen atom)

15.64 g (107 mmol) of L-(+)-lysine were dissolved in 60 cm$^3$ of methanol and in an another 60 cm$^3$ of methanol 20 g (107 mmol) of racemic 2-hydroxy-2-(2-chlorophenyl)acetic acid were dissolved. These two solutions were combined and heated till the total dissolution to 40-45° C. The mixture was seeded with L-(+)-lysine salt of (R)-(−)-2-hydroxy-2-(2-chlorophenyl)acetic acid at 40° C. The mixture was stirred at 40° C. for two hours and at 30° C. for two hours, then it was filtered and the precipitated substance was washed with methanol and dried thus 9.44 g of (R)-(−)-2-hydroxy-2-(2-chlorophenyl)acetic acid-(L)-(+)-lysine salt were obtained. This obtained dry salt was dissolved in 10 cm$^3$ of water and it was acidified with 5.4 cm$^3$ of 37% hydrochloric acid and extracted with methyl-tert.-butylether. The extract was dried on sodium sulfate and concentrated: 5.3 g of R-(−)-2-hydroxy-2-(2-chlorophenyl)acetic acid were obtained, ($[\alpha]_D^{20}=-153.8°$ (c=4, methyl alcohol), optical purity is 98%) which was recrystallized with toluene (42 cm$^3$) and it was filtered off at 60° C. and covered with toluene.

5.2 g (27.86 mmol) of (R)-(−)-2-hydroxy-2-(2-chlorophenyl)acetic acid were received after drying. Yield: 26% $[\alpha]_D^{20}=-157°$ (c=4, methyl alcohol).

The mother liquor of the resolution was concentrated, dissolved in 40 cm$^3$ of water, acidified with 13.2 cm$^3$ of 37% hydrochloric acid and it was extracted with methyl-tert.-butyl ether. After evaporation 13.9 g (74.54 mmol) of enantiomeric mixture rich in (S)-(+)-2-hydroxy-2-(2-chlorophenyl)-acetic acid were obtained, ($[\alpha]_D^{20}=+57°$ (c=4, methyl alcohol) which was racemisable and recyclable into the process.

EXAMPLE 4

Racemisation 13.5 g of enantiomeric mixture rich in (S)-(+)-2-hydroxy-2-(2-chlorophenyl)-acetic acid obtained in Example 3 were dissolved in 24 cm$^3$ of water and it was alkalized with 11.56 g (289 mmol) of sodium hydroxyde, 2.4 cm$^3$ of dimethylsulfoxide were added and the mixture was stirred for 5 hours at 100° C.

The received reaction mixture was diluted with 20 cm$^3$ of water and acidified with 24.3 cm$^3$ of 37% hydrochloric acid (289 mmol) and it was extracted with methyl-tert.-butyl ether.

Extract was dried, clarified with 1.5 g of activated charcoal, filtered, concentrated and recrystallized from 17.4 cm$^3$ of toluene at 5° C., after filtering it was washed with toluene. The substance obtained after drying was 12.8 g (68.6 mmol) of 2-hydroxy-2-(2-chlorophenyl)acetic acid ($[\alpha]_D^{20}=0.0°$ (c=4, methyl alcohol).

Figure 2:
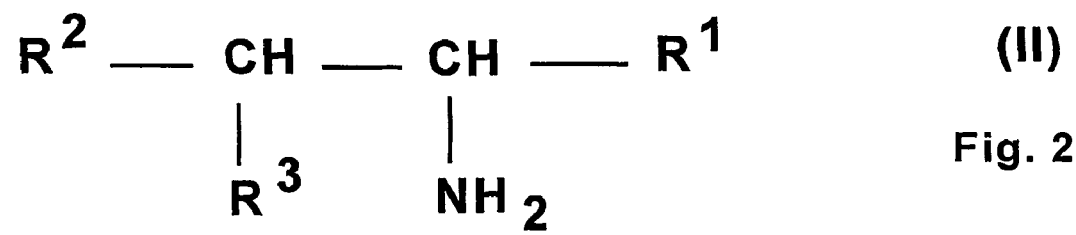

FIG. 1 shows the compound of formula (I) and FIG. 2 shows the compounds of the general formula (II).

The invention claimed is:

1. Process for the preparation of (R)-(−)-2-hydroxy-2-(2-chlorophenyl)acetic acid of formula I:

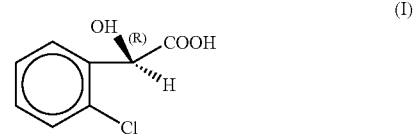

(I)

wherein racemic 2-hydroxy-2-(2-chlorophenyl)acetic acid is resolved with a substituted amine of formula (II):

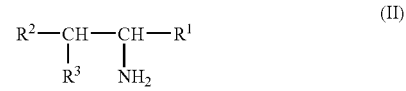

(II)

where $R^1$ means hydroxy-methyl group or carboxyl group, $R^2$ means phenyl group, nitro-phenyl group or a $C_1$-$C_4$ alkyl group substituted with an amino group, $R^3$ means hydroxyl group or hydrogen atom.

2. Process according to claim 1, wherein the substituted amine is (1S, 2S)-(+)-1-phenyl-2-amino-1,3-propanediol.

3. Process according to claim 1, wherein the substituted amine is (1R, 2R)-threo-(−)-1-(4-nitrophenyl)-2-amino-1,3-propanediol.

4. Process according to claim 1, wherein the substituted amine is L-(+)-lysine.

5. Process according to claim 1, wherein the (S)-(+)-2-hydroxy-2-(2-chlorophenyl)acetic acid obtained by resolution is racemised and then it is returned to the resolution process.

6. (1S, 2S)-(+)-1-phenyl-2-amino-1,3-propanediol(S)-(+)-2-hydroxy-2-(2-chlorophenyl)acetic acid salt.

7. (1R, 2R)-(−)-threo-1-(4-nitrophenyl)-2-amino-1,3-propanediol (R)-(−)-2-hydroxy-2-(2-chlorophenyl)acetic acid salt.

8. Process for the preparation of (R)-(−)-2-hydroxy-2-(2-chlorophenyl)acetic acid of formula I:

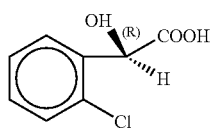
(I)

wherein racemic 2-hydroxy-2-(2-chlorophenyl)acetic acid is resolved with a substituted amine of formula (II):

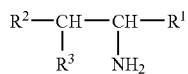
(II)

where $R^1$ means hydroxy-methyl group or carboxyl group, $R^2$ means phenyl group, nitro-phenyl group or a $C_1$-$C_4$ alkyl group substituted with an amino group, and $R^3$ means hydroxyl group or hydrogen atom; and wherein a pair of diastereomeric salts of the racemic 2-hydroxy-2-(2-chlorophenyl)acetic acid and the compound of formula (II) is formed in an organic solvent or in a mixture of water and one or more organic solvents, and one of the salts of the pair of diastereomeric salts which is separated due to its different solubility from the pair of diastereomeric salts is obtained from the reaction mixture, and the compound of the formula (I) is obtained from the salt or from the mother liquor.

9. Process for the preparation of (R)-(−)-2-hydroxy-2-(2-chlorophenyl)acetic acid of formula I:

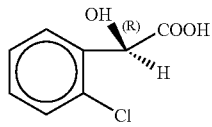
(I)

wherein racemic 2-hydroxy-2-(2-chlorophenyl)acetic acid is resolved with a substituted amine of formula (II):

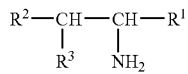
(II)

where $R^1$ means hydroxy-methyl group or carboxyl group, $R^2$ means phenyl group, nitro-phenyl group or a $C_1$-$C_4$ alkyl group substituted with an amino group, and $R^3$ means hydroxyl group or hydrogen atom; and wherein the optical purity of the crude compound of the formula (I) obtained by resolution is increased by selective crystallization.

10. Process for the preparation of (R)-(−)-2-hydroxy-2-(2-chlorophenyl)acetic acid of formula I:

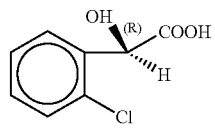
(I)

wherein racemic 2-hydroxy-2-(2-chlorophenyl)acetic acid is resolved with a substituted amine of formula (II):

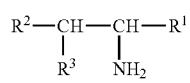
(II)

where $R^1$ means hydroxy-methyl group or carboxyl group, $R^2$ means phenyl group, nitro-phenyl group or a $C_1$-$C_4$ alkyl group substituted with an amino group, and $R^3$ means hydroxyl group or hydrogen atom; and wherein the optical purity of the crude compound of the formula (I) obtained by resolution is increased by selective crystallization; and wherein the selective crystallization is carried out in toluene or in isopropyl-acetate.

11. Process for the preparation of (R)-(−)-2-hydroxy-2-(2-chlorophenyl)acetic acid of formula I:

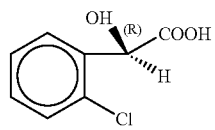
(I)

wherein racemic 2-hydroxy-2-(2-chlorophenyl)acetic acid is resolved with a substituted amine of formula (II):

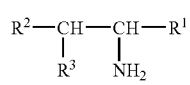
(II)

where $R^1$ means hydroxy-methyl group or carboxyl group, $R^2$ means phenyl group, nitro-phenyl group or a $C_1$-$C_4$ alkyl group substituted with an amino group, and $R^3$ means hydroxyl group or hydrogen atom; and wherein the optical purity of the crude compound of the formula (I) obtained by resolution is increased by selective crystallization; and wherein the compound of increased optical purity of the formula (I) obtained by selective crystallization is separated from the solvent at a temperature between +40° and +100° C.

12. Process for the preparation of (R)-(−)-2-hydroxy-2-(2-chlorophenyl)acetic acid of formula I:

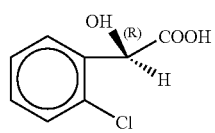
(I)

wherein racemic 2-hydroxy-2-(2-chlorophenyl)acetic acid is resolved with a substituted amine of formula (II):

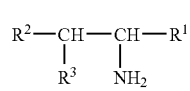
(II)

where $R^1$ means hydroxy-methyl group or carboxyl group, $R^2$ means phenyl group, nitro-phenyl group or a $C_1$-$C_4$ alkyl group substituted with an amino group, and $R^3$ means hydroxyl group or hydrogen atom; and wherein the (S)-(+)-2-hydroxy-2-(2-chlorophenyl)acetic acid obtained by resolution is subjected to racemisation and then it is returned to the resolution process; and wherein the racemisation is carried out with an alkali metal hydroxide.

13. Process for the preparation of (R)-(−)-2-hydroxy-2-(2-chlorophenyl)acetic acid of formula I:

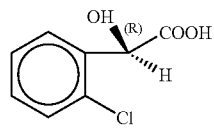
(I)

wherein racemic 2-hydroxy-2-(2-chlorophenyl)acetic acid is resolved with a substituted amine of formula (II):

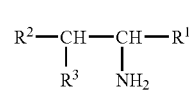
(II)

where $R^1$ means hydroxy-methyl group or carboxyl group, $R^2$ means phenyl group, nitro-phenyl group or a $C_1$-$C_4$ alkyl group substituted with an amino group, and $R^3$ means hydroxyl group or hydrogen atom; and wherein the (S)-(+)-2-hydroxy-2-(2-chlorophenyl)acetic acid obtained by resolution is subjected to racemisation and then it is returned to the resolution process; and wherein the racemisation is carried out in water in the presence of a small quantity of aprotic solvent.

14. Process according to claim 12 wherein the alkali metal hydroxide is sodium hydroxide.

15. Process according to claim 13 wherein the aprotic solvent is dimethyl sulfoxide, sulfolane, dimethyl formamide, hexamethyl phosphoric acid triamide or N-methylpyrrolidone.

* * * * *